US010639494B2

(12) United States Patent
Sun et al.

(10) Patent No.: US 10,639,494 B2
(45) Date of Patent: May 5, 2020

(54) TIME-VARYING MAGNETIC FIELD THERAPY USING MULTISTABLE LATCHING MECHANISMS

(71) Applicant: Rhode Island Board of Education, State of Rhode Island and Providence Plantations, Providence, RI (US)

(72) Inventors: Ying Sun, West Warwick, RI (US); Brian Silver, Sharon, MA (US); Tanya Wang, Cranston, RI (US)

(73) Assignee: Rhode Island Board of Education, Providence, RI (US)

(*) Notice: Subject to any disclaimer, the term of this patent is extended or adjusted under 35 U.S.C. 154(b) by 316 days.

(21) Appl. No.: 15/708,333

(22) Filed: Sep. 19, 2017

(65) Prior Publication Data
US 2018/0078780 A1    Mar. 22, 2018

Related U.S. Application Data

(60) Provisional application No. 62/396,915, filed on Sep. 20, 2016.

(51) Int. Cl.
*A61N 2/12*      (2006.01)
*A61N 2/00*      (2006.01)
(Continued)

(52) U.S. Cl.
CPC .............. *A61N 2/12* (2013.01); *A61N 2/006* (2013.01); *H01F 7/0221* (2013.01);
(Continued)

(58) Field of Classification Search
CPC ... A61N 2/12; A61N 2/06; A61N 2/00; A61B 5/05; A61B 5/4064; A61B 5/6803; A61B 5/0476
See application file for complete search history.

(56) References Cited

U.S. PATENT DOCUMENTS 6,306,076 B1 * 10/2001 Gill .......................... A61N 2/06
                                                    600/15
6,328,685 B1 * 12/2001 K.o slashed.rsgaard ....................
                                                    A61N 2/002
                                                    600/15
(Continued)

OTHER PUBLICATIONS

Colbert, A. et al., "Static Magnetic Field Therapy: A Critical Review of Treatment Parameters," Evid. Based Complement. Alternat. Med. (eCAM), vol. 6(2), 133-139 (2009).
(Continued)

*Primary Examiner* — Samuel G Gilbert
(74) *Attorney, Agent, or Firm* — Milstein Zhang & Wu LLC; Duan Wu, Esq.

(57) ABSTRACT

The invention provides wearable devices for effecting transcranial magnetic stimulation to be used by patients who have suffered brain injuries. Permanent magnets are shifted or rotated to deliver a time-varying magnetic field, preferably about the locus of the injury. In an embodiment, the strong magnetic fields of the permanent magnets are directed to the injured area for therapeutic purposes. A novel mechanism is provided that uses a small battery-powered electromagnet to interact with the weak peripheral magnetic fields of the permanent magnets and to shift the permanent magnets between two or more stable positions. As a result, a lightweight, quiet, wearable device with low power consumption is provided.

20 Claims, 11 Drawing Sheets

(51) Int. Cl.
*H01F 7/02* (2006.01)
*H01F 7/16* (2006.01)
*H01F 7/14* (2006.01)
*A61N 2/02* (2006.01)

(52) U.S. Cl.
CPC ......... *H01F 7/0273* (2013.01); *H01F 7/0294* (2013.01); *H01F 7/14* (2013.01); *H01F 7/16* (2013.01); *A61N 2/02* (2013.01)

(56) References Cited

U.S. PATENT DOCUMENTS

| | | | | |
|---|---|---|---|---|
| 6,663,557 | B2* | 12/2003 | Werny | A61N 2/12 600/15 |
| 8,936,542 | B1 | 1/2015 | Bates | |
| 2016/0193476 | A1* | 7/2016 | Helekar | A61N 2/006 600/544 |

OTHER PUBLICATIONS

Levkovitz, Y. et al., "A randomized controlled feasibility and safety study of deep tanscranial magnetic stimulation," Clin. Neurophysiol., vol. 118(12), pp. 2730-2744, (2007).

Levkovitz, Y. et al., "Deep Transcranial Magnetic Stimulation Over the Prefrontal Cortex: Evaluation of Antidepressant and Cognitive Effects in Depressive Patients," Brain Stimulation, vol. 2, 188-200 (2009).

Davis, R. et al. "Static magnetic field helmet for brain injury rehabilitation," 41st Northeast Bio-engineering Conference, Troy, NY, Apr. 17-19, (2015).

Corti, M. et al., "Repetitive Transcranial Magnetic Stimulation of Motor Cortex after Stroke: A Focused Review," Am. J. Phys. Med. Rehabil., vol. 91(3), pp. 254-270, (2012).

Sack, A. T. et al. "Optimizing Functional Accuracy of TMS in Cognitive Studies: A Comparision of Methods," J. Cogn. Neurosci., vol. 21(2), pp. 207-221, (2009).

Markov, M. et al., "Magnetic Field Therapy: A Review," Electromagnetic Biology and Medicine, vol. 26: 1-23 (2007).

Anderkova, L., et al., "Cognitive effects of repetitive transcranial magnetic stimulation in patients with neurodegenerative diseases—Clinician's perspective," J. Neurol Sci., vol. 339(1-2), pp. 15-25, (2014).

* cited by examiner

TIME-VARYING MAGNETIC FIELD THERAPY USING MULTISTABLE LATCHING MECHANISMS

CROSS-REFERENCE TO RELATED APPLICATIONS

This application claims priority to and the benefit of U.S. provisional patent application Ser. No. 62/396,915, filed Sep. 20, 2016, which application is incorporated herein by reference in its entirety.

FIELD OF THE INVENTION

The invention relates to methods and apparatuses for the rehabilitation and treatment of brain injury patients. More specifically, the invention relates to wearable devices that provide transcranial magnetic stimulation, preferably centered about an injured area. The device of the invention may be used throughout a rehabilitation session or during a daily routine.

BACKGROUND OF THE INVENTION

Traumatic brain injuries and acquired brain injuries affect millions of people each year in the United States and beyond. These injuries leave devastating symptoms, some of which could be recovered through medications and/or rehabilitation treatments.

Transcranial magnetic stimulation (TMS) is a noninvasive therapy used to stimulate local regions of the brain. It utilizes electrical currents generated in coils in order to induce magnetic fields of varying frequencies. These magnetic pulses with a strength on the order of one Tesla are then focused through specific placement on the head in order to polarize target areas of the brain. In recent years, TMS has been used to treat depression (Levkovitz, Y., et al. *Brain Stimul.*, vol. 2(4), pp. 188-200, 2009) and several neurodegenerative disease including Parkinson's and Alzheimer's (Anderkova, L., and I. Rektorova *J. Neurol Sci.*, vol. 339 (1-2), pp. 15-25, 2014), with varying degrees of success. TMS has also been studied in patients with upper limb weakness following stroke with results that suggest possible benefits (Corti, M., et al. *Am. J. Phys. Med. Rehabil.*, vol. 91(3), pp. 254-270, 2012). The effectiveness of TMS for brain injury rehabilitation has been demonstrated in several recent studies (Sack, A. T., et al. *J. Cogn. Neurosci.*, vol. 21(2), pp. 207-221, 2009; Levkovitz, Y., et al. *Clin. Neurophysiol.*, vol. 118(12), pp. 2730-2744, 2007). Stimulating nerve cells in affected area via TMS may also aid in the rehabilitation of various stroke side effects other than just limb weakness.

After a stroke, many of the patient's cognitive and motor abilities are affected. Memory and motor control in specific areas may be impaired or lost. Current TMS for stroke rehabilitation is performed solely in a hospital setting, with each session lasting about 40 minutes. This procedure is costly, limiting availability to many patients who are mobility-impaired to start with. The present invention, in an effort to find an alternative, provides a lightweight headwear for transcranial magnetic therapy over a prolonged period of application time and one that is suitable for outpatient, e.g., at-home, use.

SUMMARY OF THE INVENTION

This invention is concerned with methods and apparatuses for producing time-varying, therapeutic magnetic fields with permanent magnets. In an embodiment, a plurality of permanent magnets are embedded in a mount that can be mechanically shifted or rotated. The mount for the permanent magnets is moved to specific stable positions by energizing electromagnets to interact with the permanent magnets momentarily. Once the mount is latched to a specific stable position, no energy is required to energize the electromagnets. The juxtaposition of the permanent magnets produces various patterns of magnetic fields that change over time. The resulting apparatus is used as a lightweight wearable device for enhancing the rehabilitation of patients with acquired brain injuries.

In one feature according to the invention, small electromagnets are used to control the positions of permanent magnets thereby providing time-varying magnetic fields for brain injury rehabilitation. In preferred embodiments, the multiple juxtapositioned patterns of magnets are stable, meaning the electromagnets are energized only during the transition in order to change and latch the pattern from one to another. The resulting wearable device is lightweight, low-noise, and low power consumption, which can provide long-duration therapeutic sessions on a daily basis.

In one aspect, the invention provides a wearable apparatus for providing magnetic therapy, said apparatus comprising at least two permanent magnets situated on a mount, and at least one electromagnet situated proximate to said permanent magnets, said electromagnet being electrically connected to a power source though a switch that is in turn controlled by a controller, said controller being programed to operate said switch to flip polarity of said electromagnet in a pattern such that said electromagnet is able to actuate continued motion in said permanent magnets without using a motor, thereby providing time-varying magnetic field for therapeutic use. In an embodiment, said mount is housed in a housing that is in turn attached to a helmet or headband for wearing on the head. In one feature, the apparatus of the invention further includes a ball bearing attached to said mount for facilitating its association with said housing. In one feature, the apparatus of the invention is configured to contain at least two stable positions for said permanent magnets such that energy required for moving said permanent magnets is reduced.

In another aspect, the invention provides a headwear for mounting on or around a human patient's head, comprising a housing that houses at least two permanent magnets, and a portable power source electrically connected to at least one electromagnet via a cross switch, said permanent magnets configured to move between at least two pre-configured stable positions as a result of magnetic interaction with said at least one electromagnet, wherein a controller pulses said at least one electromagnet with appropriate timing to switch the polarity of said at least one electromagnet that actuate a continued motion in said at least two permanent magnets.

In another aspect, the invention provides a method for generating time-varying therapeutic magnetic fields with permanent magnets by aiming its strong fields towards the treatment area and using secondary electromagnets to interact with weak peripheral fields of said permanent magnets for creating mechanical movements in said permanent magnets. The method may further include the step of switching the polarity of said secondary electromagnets so that their effect on the weak peripheral fields of said permanent magnets results in said mechanical movements.

In another aspect, the invention provides a method of differential stimulations of the brain by using two sets of permanent magnets moving at different velocities with one set positioned over an injured area of the brain and the other set positioned over an other area of the brain. In one feature, the other area of the brain is uninjured.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DESCRIPTION OF THE INVENTION

Figure 1:
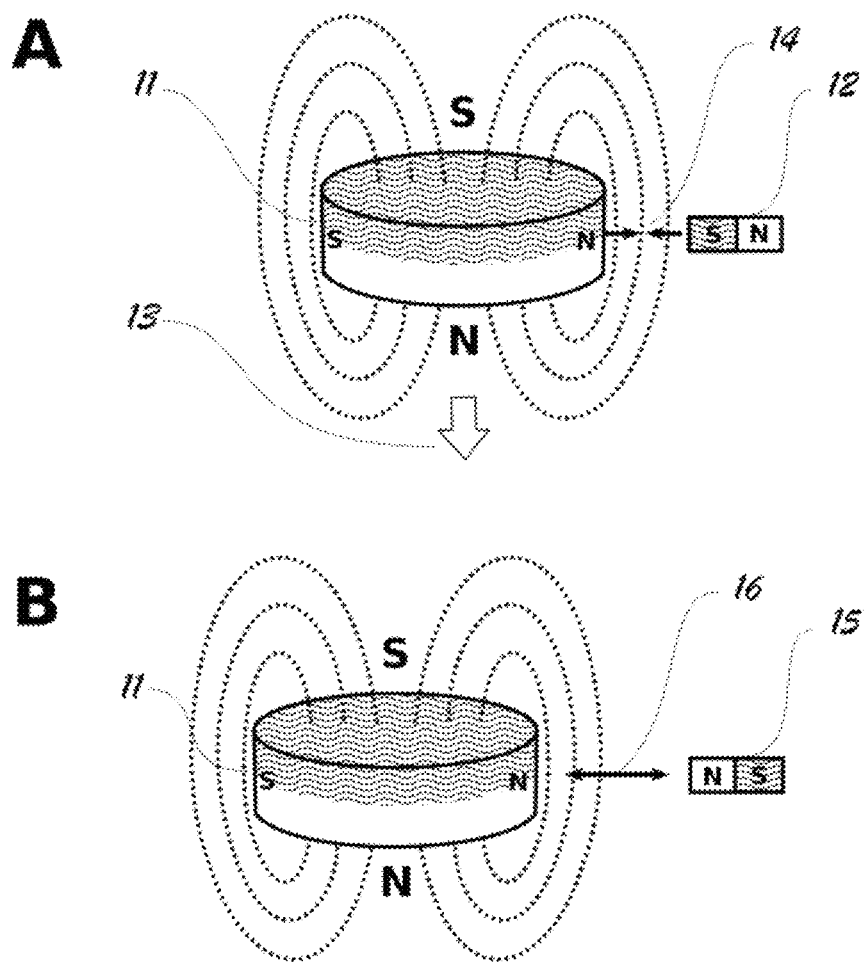
FIG. 1. Panel A is an illustrative diagrammatic view of a disc magnet with its strong magnetic field directed toward a therapeutic target and its fringe weak magnetic field attracted to a small electromagnet on the right. Panel B shows that the disc magnet is being pushed away as the polarity of the electromagnet is switched.

The present invention is concerned with methods and apparatuses using juxtapositioned permanent magnets for rehabilitation treatments of acquired brain injuries such as stroke. The apparatuses, called MagnetPeutics in some embodiments, are battery-powered headwear without being tethered to an electric outlet or a control unit such that it can be worn comfortably for hours. The invention has been made possible by the recent advancement in neodymium permanent magnets, which can produce magnetic field strengths on the order of 1 Tesla. Lithium-ion batteries have also been significantly advanced recently. However, an electromagnet driven by a battery and of a wearable weight is on the order of 1 m Tesla, which is far too weak for purpose of rehabilitation of brain injuries.

In addition to the magnetic field strength, another factor needed for effective stimulation of neurons in the brain is the speed at changing the magnetic field. The transcranial magnetic stimulation (TMS) uses strong electromagnets that can change their fields very fast. However, TMS uses a technology similar to that of the magnetic resonance imaging (MM), which requires the patients tethered to the machine and cannot be made wearable. The permanent magnet has a fixed magnetic field; the only way to make it time-varying is to change the position of the magnet mechanically. Table 1 below summarizes the differences between TMS and apparatus embodiments of the invention, MagnetPeutics.

TABLE 1

|  | Strength | Frequency | Session Time | Duration |
|---|---|---|---|---|
| TMS | 1 Tesla | 10 Hz | 1 hr/wk | weeks |
| MagnetPeutics | ⅓ Tesla | 1 Hz | 8 hrs daily | months |

This invention provides at least the following solutions to overcome three technical difficulties that would have prevented the development of an effective headwear for magnetic stimulation:

1) Multistable latching mechanism: The multistable latching mechanism is a design that allows a magnet assembly to have two or more stable positions. The transition from one position to another is done by momentarily energizing a small electromagnet. A stable position is "latched" in the sense that no energy is required to maintain in that position.

2) Dual uses of the magnetic field: The strong magnetic field generated by the permanent magnet is directed toward the therapeutic target such as a brain injury. The weaker magnetic field on the peripheral region of the same magnet is used to interact with an electromagnet for actuating spacial change. Thus, the magnet field required from the electromagnet to actuate the desired spacial change is much weaker and does not require a strong current to produce.

3) Motorless design: Mechanical movements are achieved by using small electromagnets to interact with the fringe magnetic fields of the permanent magnets without using an off-the-shelf motor or actuator. Thus, this design is different from the conventional approaches that employ motors. Motors are in general heavy, bulky, noisy, expensive, and high on power consumption.

FIG. 1 demonstrates the two different uses of the magnetic field of a permanent magnet. Panel A shows a permanent, disc magnet 11 with its weak fringe magnetic field attracted to a small electromagnet 12. The strong magnetic field coming off the flat surfaces of the magnet 11 is directed toward a therapeutic target 13. The polarity of the electromagnet 12 is set to lead to a movement 14 where the electromagnet 12 attracts the disc magnet 14. Panel B shows that the polarity of the electromagnet 15 is switched, resulting in a movement 16 where the disc magnet is pushed away.

Figure 2:
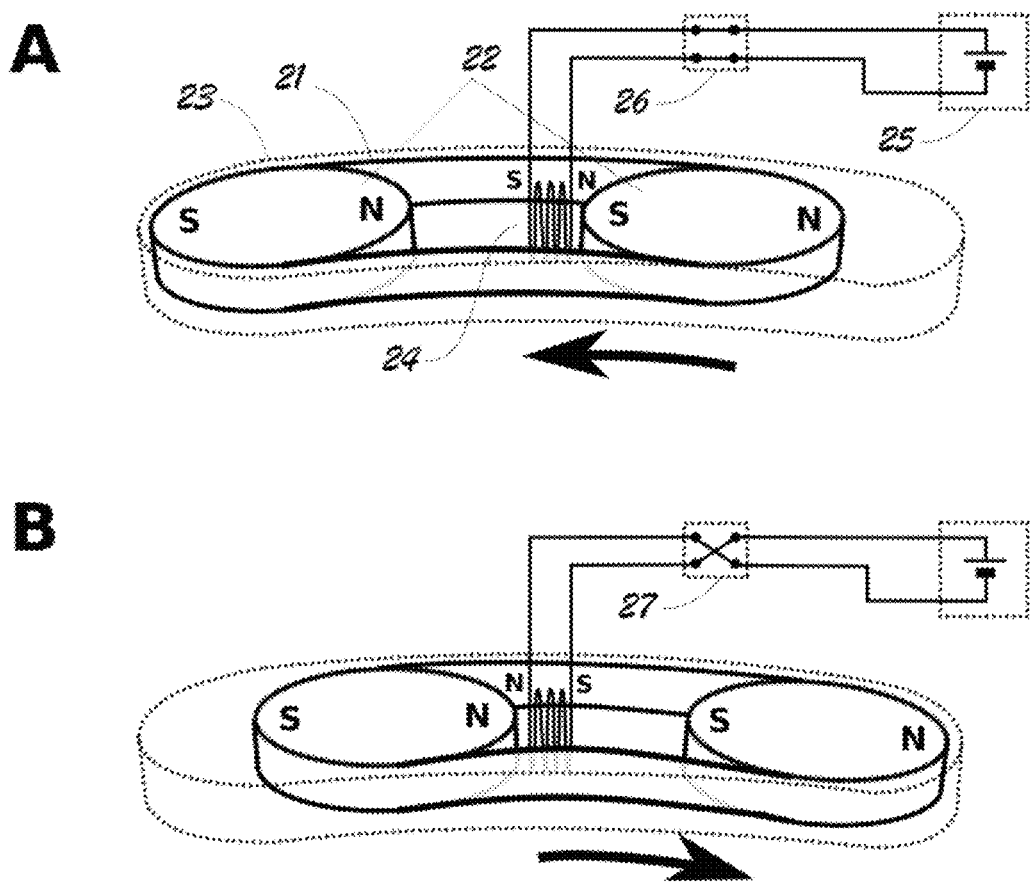
FIG. 2. Panel A illustrates a sliding mechanism containing two disc magnets with an in-between coil serving as an actuator. Panel B shows that the magnets are shifted to another stable position by changing the direction of the current flow in the coil.

Referring now to FIG. 2, in an exemplary embodiment according to the invention, a bistable sliding mechanism is provided. Specifically, a mount 21 that carries two permanent disc magnets 22 can slide freely in a mount 23. The mount can be shifted back and forth between two stable positions, e.g., along a linear or curved track. A small coil (electromagnet) 24 is positioned between the two permanent disc magnets. To shift the mount, the coil is energized momentarily by a battery 25 via a cross switch 26. When the cross switch changes the direction of the current flowing through the coil, so does the polarity of the electromagnet 24. Once the mount 23 is moved to the desired position, no energy is further required for the electromagnet to hold the mount at that position. By changing the polarity of the electromagnet, the mount can be latched to one of the two stable positions. Panel B shows that the cross switch 27 is set to the alternative position. As a result, the change in the polarity of the electromagnet causes the disc magnets and its mount to slide to the other stable position on the right side.

Figure 3:
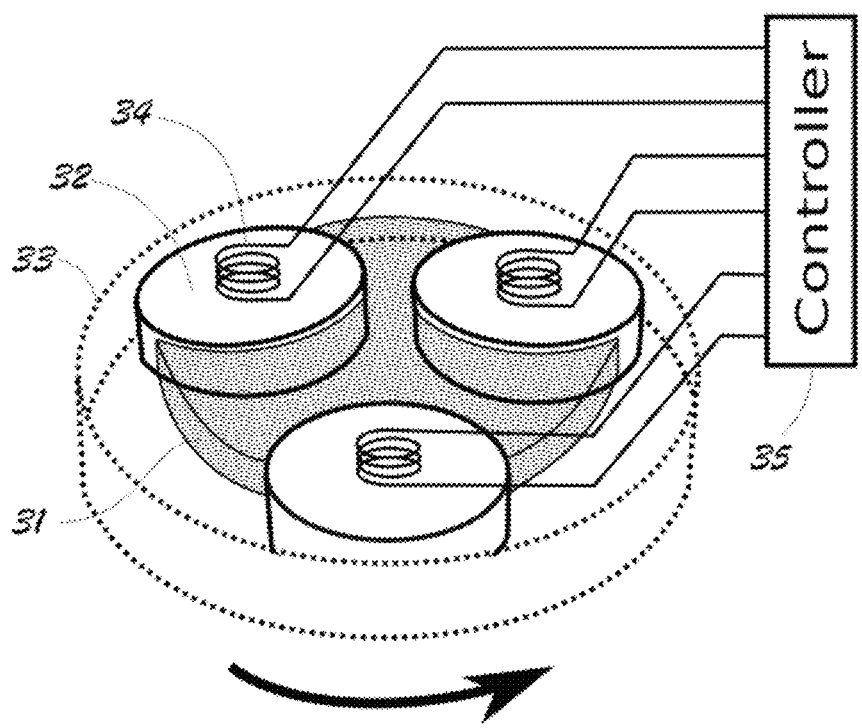
FIG. 3 illustrates a rotating mechanism containing three disc magnets.

Referring now to FIG. 3, in another exemplary embodiment according to the invention, a tristable rotating mechanism is provided. This embodiment employs a rotating mechanism. Three permanent disc magnets 32 are embedded in a rotatable circular mount 31, enclosed in a stationary housing 33. The mount can be moved to one of three stable positions through the use of three electromagnets 34 that interact with the magnetic fields of the permanent disc magnets. Each of the electromagnets is energized by a controller 35 with appropriate timing.

Figure 4:
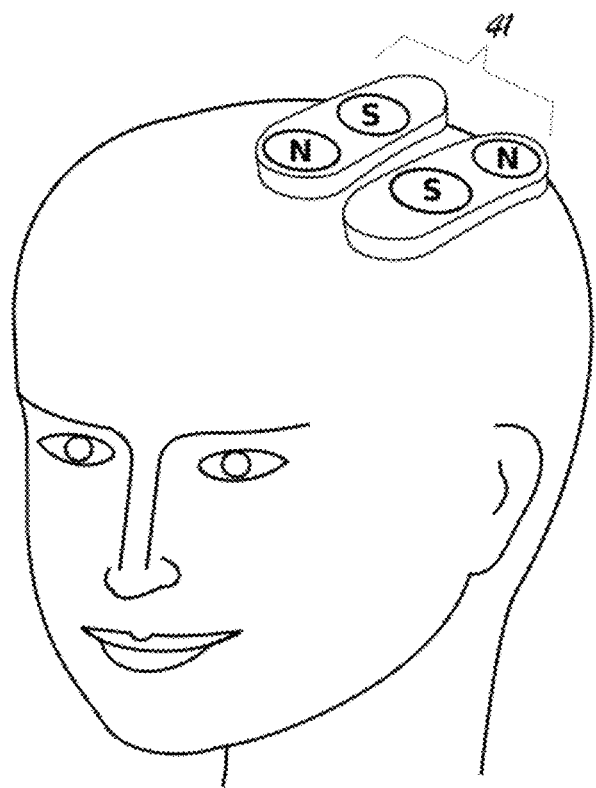
FIG. 4 illustrates a pair of sliding mechanisms positioned on the head of a patient for therapeutic purposes.
Figure 5:
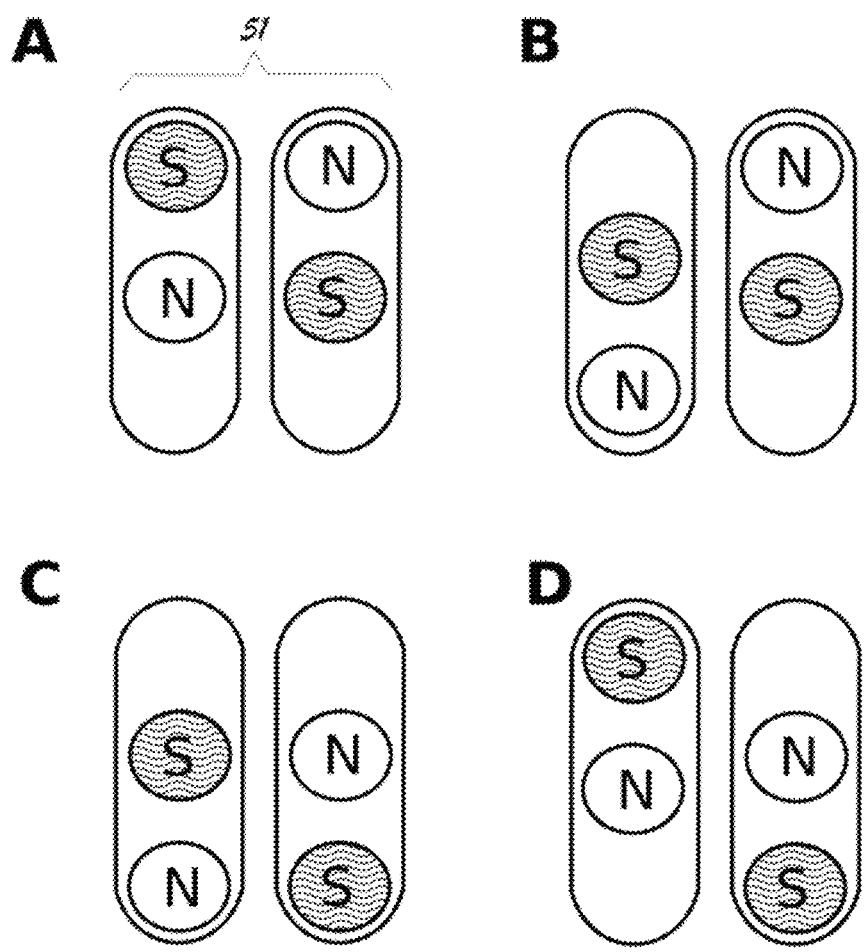
FIG. 5. Panels A-D illustrate the four different stable positions of the magnets for two sliding mechanisms each containing two disc magnets.

FIG. 4 shows an application of the invention for providing transcranial magnetic stimulation over an area of an acquired brain injury such as stroke. Two sliding units 41 are used to provide a juxtaposition of four permanent disc magnets. The two disks within the said units are shifted at various frequencies to allow for the spacial changes as well as the temporal changes of the magnetic field. As shown in FIG. 5 (panels A-D), with two sliding units 51, a total of four juxtaposition patterns with different latching positions for the permanent magnets can be achieved.

Figure 6:
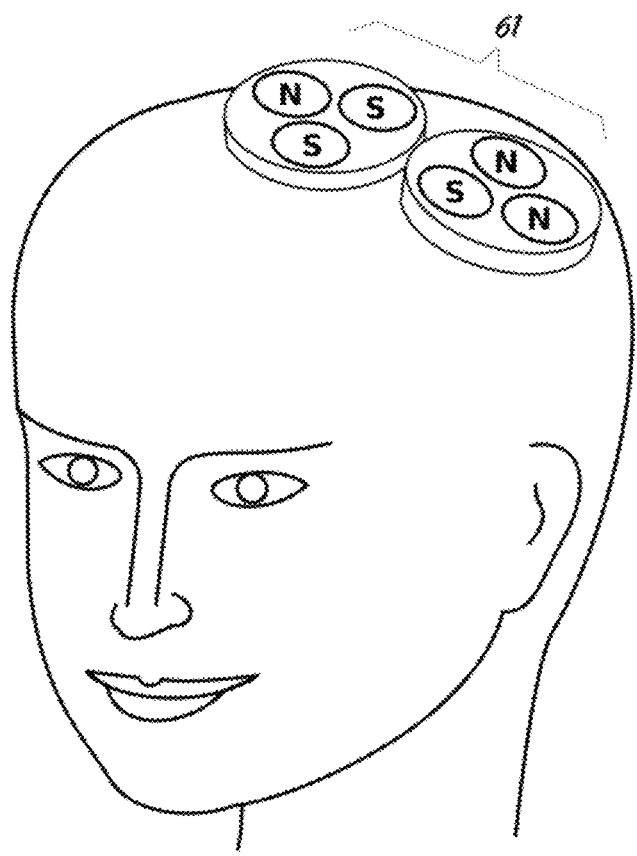
FIG. 6 illustrates a pair of rotating mechanisms positioned on the head of a patient for therapeutic purposes.
Figure 7:
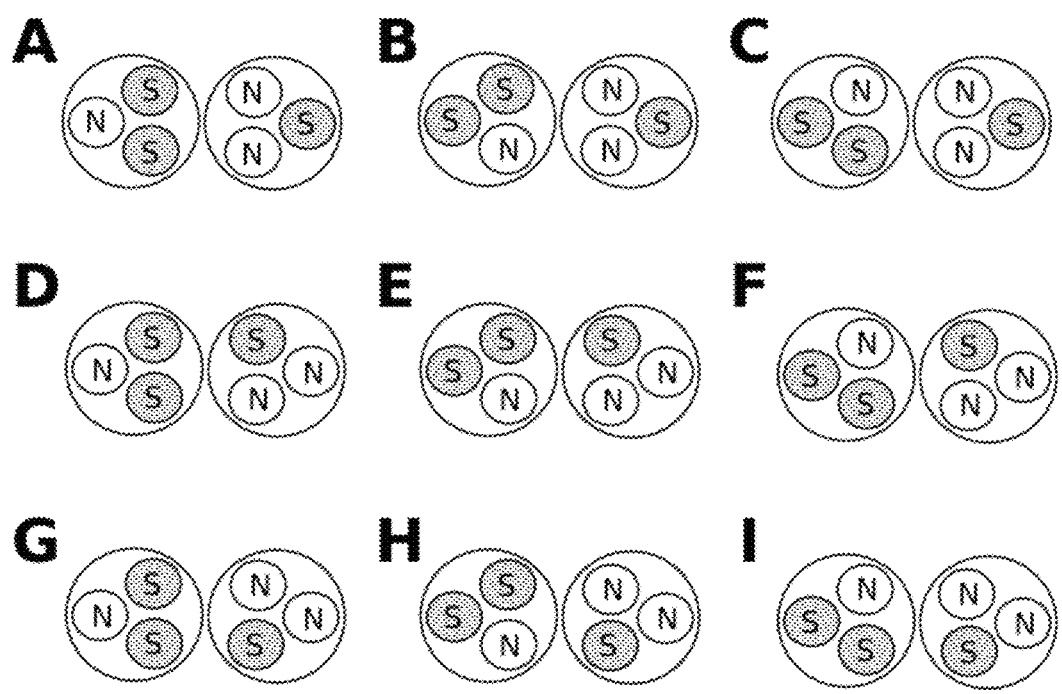
FIG. 7. Panels A-I illustrate the nine different stable position patterns of the magnets for two rotating mechanisms each containing three disc magnets.

FIG. 6 shows a pair of the rotating units 61 positioned on the head of a patient for therapeutic purposes. Each of the rotating mechanisms has 3 stable positions. A time-varying magnetic field is created by rotating each of the two magnet assemblies among the three stable positions. As shown in FIG. 7 (panels A-I), with two rotating units a total of nine juxtaposition patterns, with different latching positions for the permanent magnets, can be achieved. Switching through these multistable latching positions allows for the delivering of complex stimulation patterns both in space and in time.

Figure 8A:
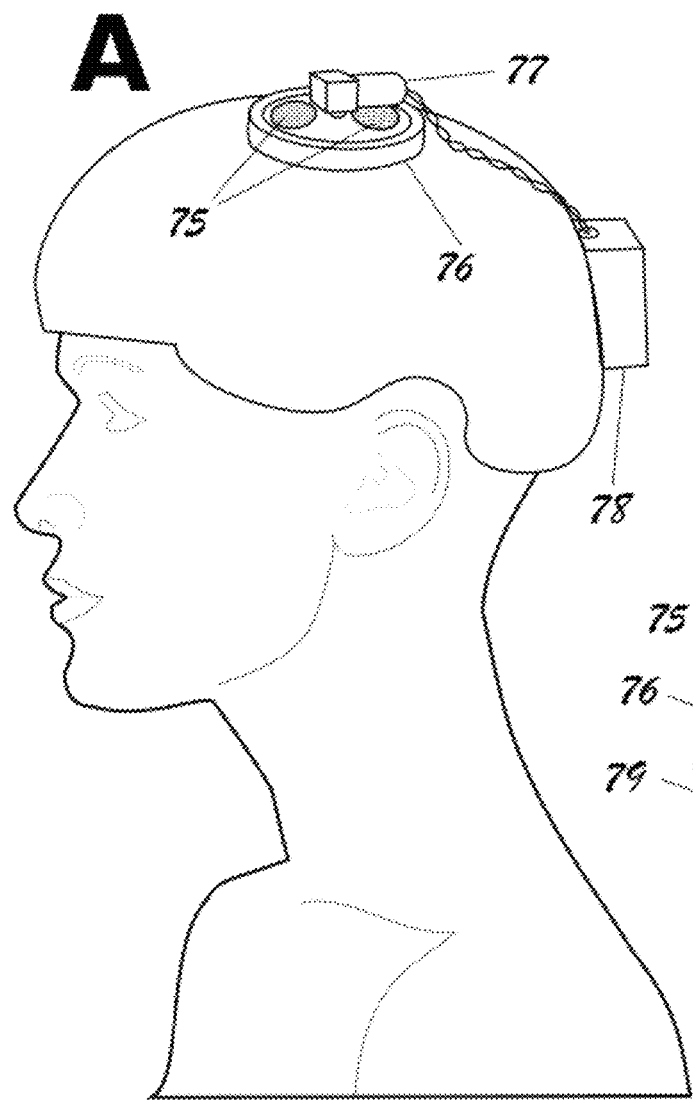
FIG. 8A illustrates a headwear embodiment of the invention using a rotating mechanism with two permanent disc magnets.
Figure 8B:
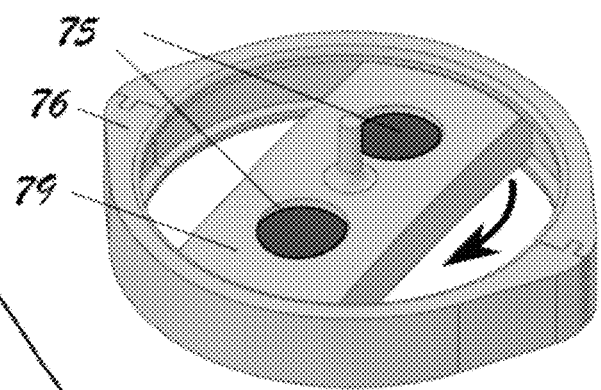
FIG. 8B provides a closer perspective view of part of the mechanism.

Referring now to FIGS. 8A and 8B, in an embodiment of the invention, a rotational mechanism was employed to achieve a faster and continuous circular motion of the permanent magnets. As shown in FIG. 8A, a magnetic therapeutic probe was positioned on the head with the support of a lightweight helmet. The placement of the therapeutic probe in the helmet was preferably flexible enough to target a specific injury area of the brain, such as the frontal lobe, the temporal lobe, parietal lobe, and occipital lobe.

As shown, two permanent magnet discs 75 were inserted into two openings in a holder 79. The holder 79 was in turn fitted to a circular housing 76 that supports rotational motion. A microprocessor was used for controlling the timing and the therapeutic protocol. The magnets were rotated through the use of a DC motor 77. A pulse width modulator was used to control the speed of the motor.

In an example representing the embodiment shown in FIGS. 8A and 8B, the mounting holder and housing were 3D-printed in ABS plastic by using a MakerBot Replicator 2× (Brooklyn, N.Y.). The permanent magnets used were N52 neodymium discs of 1 inch diameter and ¼ inch in thickness. The magnetic flux density normal to the surface was 0.33 T at the center of the disc, and 0.52 T on the perimeter. The holder was continuously rotated by using a 12V DC motor (Model JSX330-370, Dmiotech) with a rated torque of 4 Kg·cm, a gear-down ratio of 330:1, and a maximum no-load speed of 24 rpm.

The control unit was developed around a PIC18F4525 microprocessor by using an ICD3 in-circuit programmer and the MPLab Integrated Development Environment (Microchip, Chandler, Ariz.). The electronics were initially developed on a breadboard and can be converted to a printed circuit board. The electronics and the DC motor were powered by use of two 9V batteries to achieve a maximum voltage of 18V.

Figure 9:
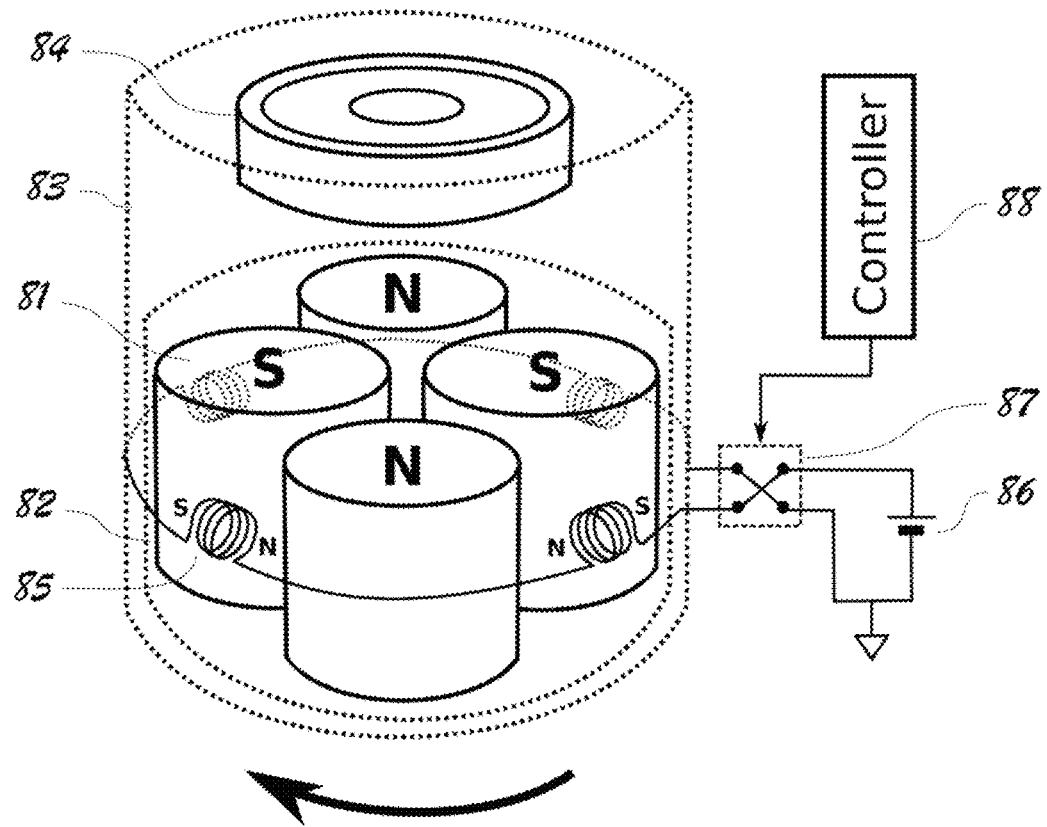
FIG. 9 illustrates a preferred embodiment also using a rotating mechanism for achieving fast and quiet rotation of the magnets through the use of a ball bearing.
Figure 10:
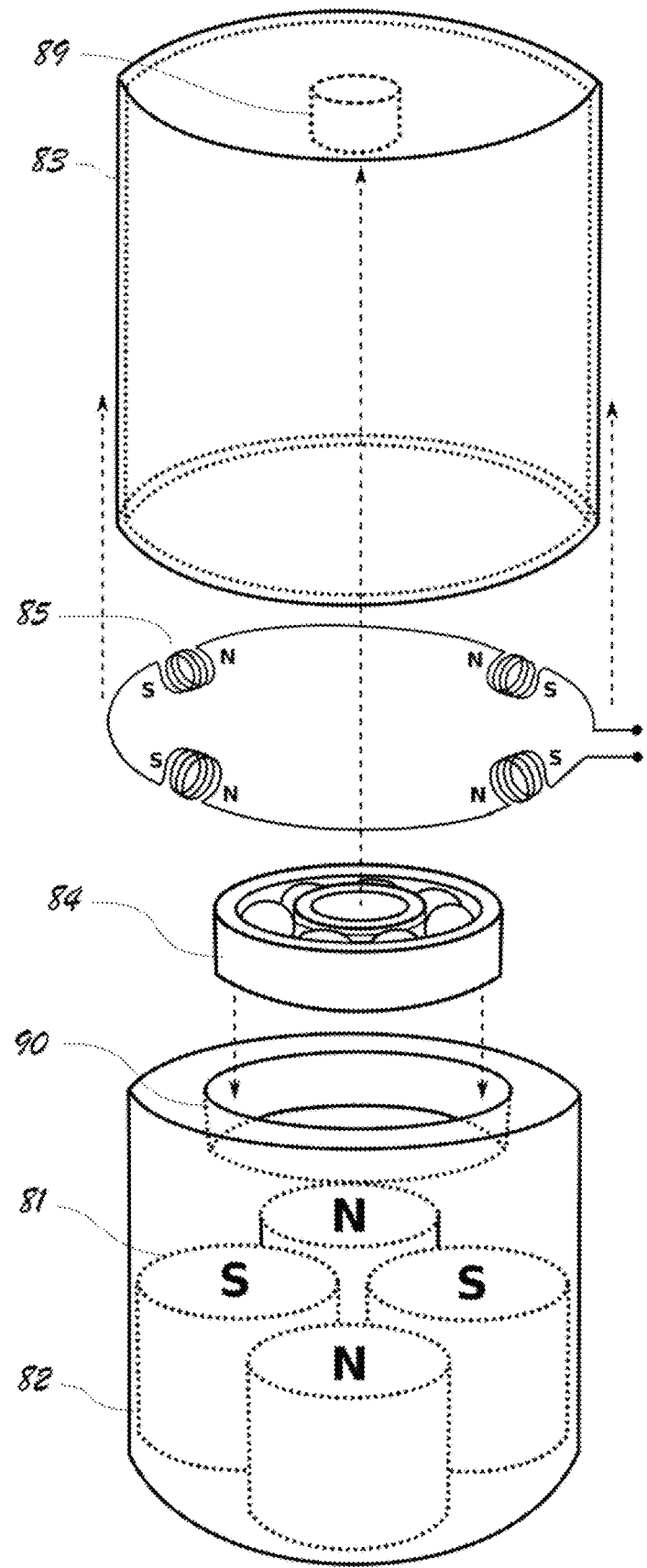
FIG. 10 provides an exploded view of the embodiment of FIG. 9.

Referring now to FIGS. 9 and 10, in yet another exemplary embodiment according to the invention, a rotating mechanism preferably with multiple stable latching positions (e.g., four in the illustrated embodiment) is provided. This embodiment is intended for achieving fast and quiet rotation of the permanent magnets with the help of a ball bearing 84. Multiple (e.g., four) cylindrical-shaped magnets 81 are enclosed in, preferably attached to, a rotatable mount 82. Better viewed in FIG. 10, the mount 82 is fitted into a stationary housing 83 via a ball bearing 84 as follows: the mount 82 has an opening or crater 90 on its top that fictionally engages or is otherwise bonded or affixed to the outer ring of the ball bearing 84. The inner ring of the same ball bearing 84, is in turn fitted over (fictionally engages or otherwise affixed to) a protruding hub 89 that is part of the stationary housing 83. As a result, as shown in FIG. 9, the ball bearing 84 facilitates the hosting/shielding of a spinning mount 82 inside a stationary housing 83.

The stationary housing 83 is in turn mounted over a headwear (e.g., a helmet or headband) for a patient to wear around the head. A preferred material for the ball bearing 84 is ceramic in order to eliminate dragging force that would have resulted from the magnets had the bearing been magnetizable metal. For instance, commercially available ball bearings such as the ones used in skateboard, inline skates and the Fidget Spinners can be used in this embodiment.

Four electromagnets (metal coils 85) are positioned around the housing 83 to turn the magnet mount 82. The coils are driven by a power source, here a battery 86 (e.g., lithium-ion batteries) via an electric cross switch 87. The cross switch, e.g., an H bridge, is operated by a controller 88 that can program when and how frequently the cross switches are flipped. When the controller first turns on the electromagnetic coils 85, they generate magnet fields strong enough to interact with the weak fringe magnetic fields around those permanent magnets 81 such that the permanent magnets 81 are put in motion. As the permanent magnets 81 move, however, their fringe magnetic fields move with them—a south pole from a first permanent magnet that originally attracted it to a particular coil's north pole now gives way to a north pole from a second permanent magnet. The controller 88 is programed to flip/switch the cross switch 87 at that moment so that the direction of the current through the four coils 85 switches, reversing the polarities of these electromagnetic coils, thereby continue to move the permanent magnets 81 in the same rotational direction (see FIG. 9). This results in the rotation of the four permanent magnets 81, bringing the mount 82 spinning about itself from one stable position to the next, utilizing minimal amount of energy.

By pulsing the cross switch 87 with appropriate timing, the magnet mount 82 spins continuously. One of the novelties of this design is that it achieves a spin motion of the magnet mount 82 without using a motor, but relies solely on the changing magnetic fields surrounding the permanent magnets. The use of a motor would have several disadvantages for a headwear device including weight, size, cost, noise, and power consumption. Besides being programed or otherwise configured to operate the cross switch 87 in a pattern such that the electromagnetic coils 85 are able to effectuate continued motion in the permanent magnets, the controller 88 is also capable of adjusting the spinning speed of the magnet mount 82 as well. This provides a way to fine-tune the frequency of the time-varying magnetic fields given off by the permanent magnets in order to achieve various therapeutic results. In a preferred embodiment of the invention, the frequency of the therapeutic magnetic field reached about 3.0 Hz and above. A "continued" motion, as used herein, does not have to be continuous and can include pauses. In one embodiment, a continued motion includes returning to a starting position at least once, preferably multiple times. In a preferred embodiment, the continued motion is continuous. Note embodiments of the invention, as in this one, are not always required to engineer stable positions for the moving permanent magnets.

Figure 11:
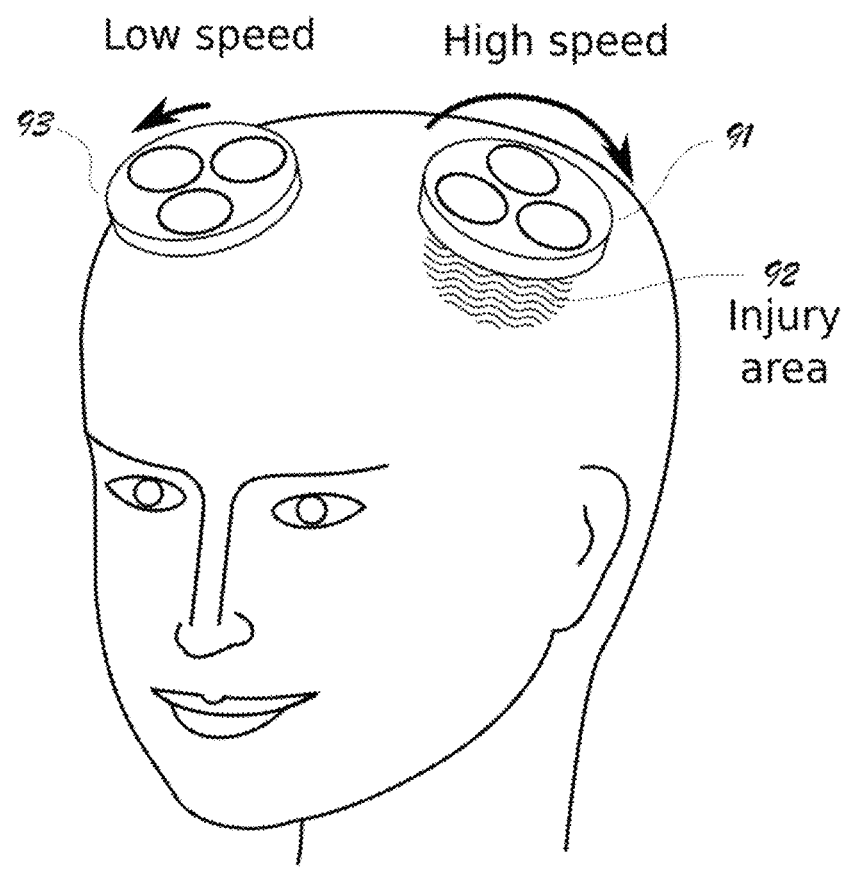
FIG. 11 illustrates an application of differential stimulations by using a faster rotating mechanism over an injured area and a slower rotating mechanism on a different area in the patient.

Referring now to FIG. 11, in an embodiment of the invention, a device can be constructed such that the permanent magnet units can be controlled to rotate at different speeds to create either excitatory or inhibitory effects. Such effects can be alternated depending on how the device is controlled or programed. For example, unit 91 rotating at a higher speed is positioned over an injury area 92 of the frontal lobe of the left brain. Another unit 93 rotating at a lower speed is positioned over a normal area of the frontal lobe of the right brain. This arrangement illustrates a platform that differential stimulations could create the potential inhibitory/excitatory effects during the process of brain rehabilitation. Further, parameters can be optimized including the juxtaposition patterns, frequency of changes, combination and synchronization of targeted treatment areas (left/right, frontal/temporal/parietal/occipital).

While the present invention has been particularly shown and described with reference to the structure and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

What is claimed is:

1. A wearable apparatus for providing magnetic therapy, said apparatus comprising:
   at least two permanent magnets situated on a mount, and at least one electromagnet situated proximate to said permanent magnets, said electromagnet being electrically connected to a power source though a switch that is in turn controlled by a controller, said controller being programmed to operate said switch to flip polarity of said electromagnet in a pattern such that said electromagnet is able to actuate continued motion in said permanent magnets without using a motor, thereby providing time-varying magnetic field for therapeutic use.

2. The wearable apparatus of claim 1, wherein said mount is housed in a housing that is in turn attached to a helmet or headband for wearing on the head.

3. The wearable apparatus of claim 2, further comprising a ball bearing attached to said mount for facilitating its said mount's association with said housing.

4. The wearable apparatus of claim 1, wherein said mount is rotatable inside said apparatus such that when said permanent magnets are actuated to rotate, they bring said mount to spin about itself.

5. The wearable apparatus of claim 1, wherein said permanent magnets are configured to slide along a linear or curved track.

6. The wearable apparatus of claim 1, wherein said continued motion in said permanent magnets is continuous.

7. The wearable apparatus of claim 1, wherein said apparatus is configured to contain at least two stable positions for said permanent magnets such that energy required for moving said permanent magnets is reduced.

8. The wearable apparatus of claim 1, comprising at least three permanent magnets.

9. The wearable apparatus of claim 1, wherein said permanent magnets are rare-earth magnets.

10. The wearable apparatus of claim 1, wherein said power source comprises a battery.

11. The wearable apparatus of claim 1, wherein said switch is a cross switch.

12. The wearable apparatus of claim 1, wherein said permanent magnets comprise neodymium.

13. A headwear for mounting on or around a human patient's head, comprising a housing that houses at least two permanent magnets, and a portable power source electrically connected to at least one electromagnet via a cross switch, said permanent magnets configured to move between at least two pre-configured stable positions as a result of magnetic interaction with said at least one electromagnet, wherein a controller pulses said at least one electromagnet with appropriate timing to switch the polarity of said at least one electromagnet that actuate a continued motion in said at least two permanent magnets.

14. The headwear of claim 13, wherein the housing contains at least four permanent magnets rotating continuously.

15. The headwear of claim 13, wherein said at least two permanent magnets rotate among at least three pre-configured stable positions.

16. The headwear of claim 13, wherein said at least two permanent magnets are rare-earth magnets.

17. A method for generating time-varying therapeutic magnetic fields with permanent magnets having both weak peripheral and strong magnetic fields by aiming the strong fields towards a treatment area and using secondary electromagnets to interact with the weak peripheral fields of said permanent magnets for creating mechanical movements in said permanent magnets.

18. The method of claim 17, further comprising switching the polarity of said secondary electromagnets so that their effect on the weak peripheral fields of said permanent magnets results in said mechanical movements.

19. The method of claim 17, wherein said permanent magnets are rare-earth magnets.

20. The method of claim 19, wherein said rare-earth magnets comprise neodymium.

* * * * *